United States Patent [19]
Yamamoto et al.

[11] Patent Number: 5,431,917
[45] Date of Patent: Jul. 11, 1995

[54] HARD CAPSULE FOR PHARMACEUTICAL DRUGS AND METHOD FOR PRODUCING THE SAME

[75] Inventors: Taizo Yamamoto, Osaka; Kenji Abe, Nara; Seinosuke Matsuura, Souraku, all of Japan

[73] Assignee: Japan Elanco Company, Ltd., Osaka, Japan

[21] Appl. No.: 114,351

[22] Filed: Sep. 1, 1993

Related U.S. Application Data

[62] Division of Ser. No. 957,892, Oct. 8, 1992, Pat. No. 5,264,223.

[51] Int. Cl.⁶ ............................................... A61K 9/48
[52] U.S. Cl. .................................... 424/451; 424/452; 424/453; 424/456; 514/962
[58] Field of Search ............... 424/451, 452, 453, 454, 424/455, 456; 514/774, 781, 779

[56] References Cited

U.S. PATENT DOCUMENTS 4,138,013  2/1979  Okajima ............................. 206/528
4,917,885  4/1990  Chiba et al. ........................ 424/78

FOREIGN PATENT DOCUMENTS 474310    2/1972  Japan .
61-100519 5/1986  Japan .
62-266060 11/1987 Japan .

*Primary Examiner*—Thurman K. Page
*Assistant Examiner*—James M. Spear
*Attorney, Agent, or Firm*—Birch, Stewart, Kolasch & Birch

[57] ABSTRACT

A hard capsule for pharmaceutical drugs comprises a water-soluble cellulose derivative as a capsule base, a gelatinizing agent and an auxiliary for gelation. The hard capsule is prepared by preparing an aqueous solution of a capsule base containing a water-soluble cellulose derivative, a gelatinizing agent and an auxiliary for gelation, immersing a capsule molding pin in the aqueous solution of the capsule base, subsequently drawing out the molding pin from the aqueous solution of the capsule base, subjecting the aqueous solution of the capsule base attached to the outer surface of the molding pin to gelate at room temperature, and forming a capsule film on the outer surface of the molding pin.

11 Claims, No Drawings

HARD CAPSULE FOR PHARMACEUTICAL DRUGS AND METHOD FOR PRODUCING THE SAME

This application is a divisional of application Ser. No. 07/957,892, filed on Oct. 8, 1992, the entire contents of which are hereby incorporated by reference, now U.S. Pat. No. 5,264,223.

BACKGROUND OF THE INVENTION

1. Field of the Invention

The present invention relates to a hard capsule for pharmaceutical drugs, specifically a hard capsule of a lower water content and with no use of known gelatin as the base material. More specifically, it relates to a hard capsule for pharmaceutical drugs using a water-soluble cellulose derivative as the base, and a method for producing the same.

2. Prior Art

As has been known, hard capsules for pharmaceutical drugs are molded from film compositions, wherein gelatin is generally used as the base material to which are added a plasticizer such as glycerin and sorbitol, and optionally, an opaquer, a dye or pigment. Such capsules generally contain about 10 to 15% by weight of water in the capsule film thereof.

If the water content in the capsule film decreases to be less than 10% by weight, the plasticity of the film is lost, resulting in the distinctive deterioration of the impact resistance during the filling process of drugs into the capsules with the outcome of no endurability of the use thereof. Irrespective of emptiness or fillingness of drugs, the film shrinks when the water content in the film is decreased during the storage of the capsules, inevitably involving the loosening of the engagement of the caps with the capsule bodies over time. Therefore, it is essential that such known gelatin hard capsules should contain a given amount of water as has been described above.

However, such gelatin hard capsules may induce disadvantages including the reduction of the titers, deterioration and color change of drugs filled therein and the insolubility of the capsule film, because the drugs are decomposed by the water contained in the capsule film if the drugs filled therein are readily hydrolyzed or two or more drugs with interactive activity to each other are contained therein.

In order to overcome these drawbacks, there have been made a variety of improvement and propositions over hard capsules for pharmaceutical drugs. For example, Japanese Patent Publication No. 47-4310 discloses a method for producing a hard capsule comprising using as a base material a water-soluble cellulose ether which is produced by substituting a part or all of the hydroxyl groups of cellulose with an alkyl group or a hydroxyalkyl group, immersing a molding pin in the water-soluble cellulose ether solution, thereby forming a capsule film. Japanese Patent Laid-Open Nos. 61-100519 and 62-266060 disclose a method for producing a hard capsule, comprising compounding the above-said water-soluble cellulose ether with polyvinyl alcohol (PVA), and yielding a hard capsule from such water-soluble immersing solution.

However, these capsules for pharmaceutical drugs are produced by immersing a molding pin in an immersing solution of the water-soluble cellulose derivative as the base material, heating just the molding pin or the film attached to the pin thereby effecting gelation prior to molding, so that the immersing solution of the base material is never gelatinized but the solution is then fallen down from the molding pin if heating is not done sufficiently. Thus, capsule films practically cannot be obtained. If the heating temperature is too high, disadvantages such as wrinkle induction into the films may be caused during gelation. In the latter case, a slight amount of the gel is solubilized into water when the water-soluble cellulose derivative attached to the molding is immersed in water pin at a higher temperature for gelation. Therefore, it is difficult to obtain a uniform film, and such film may frequently develop cracking during the detachment of the molded article, i.e. the capsule film after drying, from the molding pin, due to the lower jelly strength thereof. In any case, it is difficult to obtain a hard capsule for pharmaceutical drugs with a lower water content in practical sense. Further, specified apparatus and procedures are required for practicing these capsule production methods, so that the most commonly known capsule manufacturing apparatus for immersion and molding of the conventional gelatin capsules cannot be used as it is.

SUMMARY OF THE INVENTION

Under such circumstances, the present invention has been proposed, and intends to overcome the drawbacks and disadvantages of the hard capsules comprising the water-soluble cellulose derivative described above.

An object of the present invention is to provide a hard capsule for pharmaceutical drugs having no fragility under the condition of a lower humidity due to the lower water content in equilibrium in the capsule film thereby preventing the cracking of the capsule film. The drugs filled therein can be prevented from deteriorating because of the lower water content. Another object of the present invention is to provide a method for producing such a hard capsule.

According to the present invention, by using a water-soluble cellulose as a base material, and adding a gelatinizing agent and an auxiliary for gelation thereto, the gelation can be achieved at room temperature.

Thus, the present invention provides a hard capsule for pharmaceutical drugs comprising a water-soluble cellulose derivatives as a base material, a gelatinizing agent and an auxiliary for gelation.

The present invention also provides a method for producing a hard capsule for pharmaceutical drugs, comprising preparing an aqueous solution of a capsule base containing a water-soluble cellulose derivative, a gelatinizing agent and an auxiliary for gelation, immersing a capsule molding pin in the aqueous solution of the capsule base, subsequently drawing out the molding pin from the aqueous solution of the capsule base, subjecting the aqueous solution of the capsule base attached to the outer surface of the molding pin to gelate at room temperature, and forming a capsule film on the outer surface of the molding pin.

DETAILED DESCRIPTION OF THE INVENTION

For water-soluble cellulose derivatives to be used in the present invention, it is preferred a cellulose ether in which some or all of hydroxyl groups thereof are substituted with a lower alkyl group and/or a hydroxyl-lower alkyl group. Examples of the cellulose derivatives include hydroxypropylmethyl cellulose, hydroxyethyl cellulose, hydroxypropyl cellulose, hydroxyethylmethyl cellulose and the like. Among them, hydroxypropylmethyl cellulose is the most preferable in terms of film molding and mechanical strength at a condition of a lower water content.

Examples of the gelatinizing agent to be used in the present invention include carrageenan, polysaccharide of tamarind seed, pectin, curdlan, gelatin, furcellaran, agar, and the like. Among them, carrageenan is specifically preferred because it has a higher gel strength and shows excellent gelatinization property under the coexistence of a specific ion described later, and thus, it can be added at a small amount for use. The carrageenan includes three types, i.e. kappa-carrageenan, iota-carrageenan, and ramda-carrageenan. In accordance with the present invention, kappa- and iota-carrageenan having gelation ability can be preferably used.

For the auxiliary for the gelation of a gelatinizing agent, a water-soluble compound having potassium ion, ammonium ion or calcium ion including potassium chloride, potassium phosphate, calcium chloride, ammonium chloride and the like may be illustrated for kappa-carrageenan, while water-soluble compounds having calcium ion including calcium chloride and the like may be illustrated for iota-carrageenan.

As to the concentration of the immersing solution, i.e. the aqueous solution of the capsule base, during the molding or producing of the hard capsule for pharmaceutical drugs according to the present invention, a water-soluble cellulose derivative, a gelatinizing agent, and an auxiliary for gelation may be contained in ranges of 5 to 25% by weight, 0.1 to 0.5% by weight and 0.01 to 0.5% by weight, respectively.

If the concentration of the water-soluble cellulose derivative in the aqueous solution of the capsule base is less than 5% by weight, it is difficult to form a capsule film of a sufficient thickness. If the concentration of the water-soluble cellulose derivative exceeds 25% by weight, the jelly viscosity of the aqueous solution increases, resulting in the difficult molding of a uniform capsule film by the immersion methods. Therefore, it is particularly preferred that the concentration of the water-soluble cellulose derivative is 13 to 17% by weight.

If the concentration of the gelatinizing agent is less than 0.1% by weight, the aqueous solution of the capsule base attached to a molding pin is not formed into gel, thus leading to the detachment thereof from the pin. If the concentration of the gelatinizing agent exceeds 0.5% by weight, the jelly viscosity of the aqueous solution increases, resulting in not only the difficult molding of a uniform capsule film by the immersion method but also the ready occurrence of gelatinized films on the wall face of the container in which the aqueous solution of the capsule base is contained, thereby causing troubles during the molding of a capsule film. Thus, the most appropriate concentration of the gelatinizing agent is 0.15 to 0.3% by weight.

As to the concentration of the auxiliary for gelation, the use thereof less than or above the range described above brings about disadvantages as in the case of the gelatinizing agent. Therefore, the most appropriate concentration of such auxiliary for gelation is 0.05 to 0.2% by weight.

In accordance with the present invention as in the case of the known hard capsules for pharmaceutical drugs, a coloring agent such as dye and pigment, an opaquer, a flavor and the like may be added to the aqueous solution depending on the need.

The hard capsule for pharmaceutical drugs of the present invention can be produced according to the conventional immersion molding method as in the case of the known gelatin hard capsules. That is, a water-soluble cellulose derivative, a gelatinizing agent and an auxiliary for gelation, furthermore optionally a coloring agent, an opaquer, a flavor and the like, are compounded together with water to prepare an aqueous solution, in which an immersion molding pin is immersed to obtain a hard capsule according to the conventional method. The temperature of the aqueous solution of the capsule base or the immersion solution is preferably adjusted to 48° to 55° C., especially to 50° to 52° C. If the temperature of the immersion solution is outside of the range, the jelly viscosity of the immersion solution is changed slightly, with the result of no good attachment of the immersion solution to the molding pin during immersion molding. Thus, a uniform capsule film is difficult to obtain. Through subsequent processes comprising drawing out the immersion molding pin from the immersion solution, drying and detaching (removing) the film from the molding pin and cutting out the film, a hard capsule of a given size is obtained following the same processes as in the production of the known gelatin hard capsules by immersion method. In this case, the time requiring for the gelation of the immersion solution on the outer surface of the immersion molding pin is slightly longer, i.e. 30 to 60 seconds than that in the case of gelatin base which is 4 to 7 seconds.

The thus obtained hard capsule film contains 5 to 25 parts by weight, more preferably 13 to 17 parts by weight of the water-soluble cellulose derivative, 0.1 to 0.5 parts by weight, more preferably 0.15 to 0.3 parts by weight of the gelatinizing agent and 0.01 to 0.5 parts by weight, more preferably 0.05 to 0.2 parts by weight of the auxiliary for gelation. More specifically, the film contains 92 to 94% by weight of the water-soluble cellulose derivative, 0.9 to 1.2% by weight of the gelatinizing water and 0.5 to 0.6% by weight of the auxiliary for gelation. The water content in the capsule film is usually in a range of 4 to 6% by weight of the capsule film.

According to the present invention, the gelation of the aqueous solution or immersion solution can be carried out at room temperature, typically 22.5° to 25.5° C. without specific heating, and can form a flexible capsule film having a lower water content.

EXAMPLES

The present invention will now be described in details with reference to examples hereinbelow, although the present invention is not restricted thereto.

Example 1

Into 19.55 liter of distilled water at about 70° C. was added and dissolved 18.4 g of potassium chloride (the concentration of the auxiliary for gelation; 0.08% by weight), followed by addition of 39.1 g of kappa-carrageenan (the concentration of the gelatinizing agent; 0.17% by weight), which was dissolved under stirring.

Into the solution was introduced 3.45 kg of hydroxypropylmethyl cellulose (the concentration of the cellulose derivative; 15% by weight) under stirring, which was then dispersed in a hot bath. Then, the temperature of the solution was decreased down to 50° C., followed by dissolution of hydroxypropylmethyl cellulose under stirring, which was then left to stand for 7 hours prior to defoaming.

The immersion solution (aqueous solution of the capsule base) thus prepared was charged into a known gelatin capsule production system based on immersion method, and while keeping the temperature of the immersion solution at 50° to 52° C., a hard capsule (Size No. 2) was obtained according to the conventional method. The following tests were conducted for evaluating the resulting capsule.

Test - 1

Assessment of Cracking of Empty Capsules

The hard capsule obtained in the Example of the present invention and a gelatin hard capsule as a control capsule were left to stand under the condition of 12% RH for 4 days at 25° C. to decrease the water content in the individual films to 1.1% and 8.8%, respectively. Separately, the same hard capsules were dried at 105° C. for 2 hours to adjust the water content in the individual films to 0%. By further subjecting the resulting samples to drop-weight impact test (wherein a 49.7 g weight is dropped down from the height of 20 cm) and finger-pressure test, the state of cracking was observed.

The results are shown in Table 1. The results clearly indicate that the hard capsule of the present invention does not crack so readily as the gelatin hard capsule.

TABLE 1

| Capsule | Drop - weight impact test | | Finger - pressure test | |
|---|---|---|---|---|
| | number of cracking per 50 | water content of capsule | number of cracking per 10 | water content of capsule |
| Invention product | 0 | 1.1% | 0 | 0% |
| Control product | 46 | 8.8% | 10 | 0% |

Test - 2

Assessment of Water Content in Equilibrium of Capsule Film

The hard capsule obtained in the Example of the present invention and the control gelatin hard capsule were left to stand for 10 days under the condition of a humidity of 43% RH and a temperature of 25° C. After it was confirmed that the equilibrium was achieved, the water content in the capsule films was determined by the method based on the loss in weight on drying, to examine the water content in equilibrium of the capsule films.

The results are shown in Table 2. The results indicate that the hard capsule of the present invention clearly has a lower content than the gelatin hard capsule and thus is a lower water content capsule.

TABLE 2

| Capsule | Water content in equilibrium |
|---|---|
| Invention product | 4.3% |
| Control product | 13.9% |

Test - 3

Assessment of Solubility of Empty Capsules

The hard capsule obtained in the Example of the present invention and the control gelatin hard capsule were subjected to solubility test under the standard condition defined by Japanese Pharmacopoeia, using distilled water heated to 37°±1° C.

The results are shown in Table 3. The results indicate that the hard capsule of the present invention clearly shows a slower solubility than the gelatin hard capsule, but achieves the solubilization within 10 minutes as defined by the Pharmacopoeia, so no trouble may be caused thereby.

TABLE 3

| Capsule | Solubilization time | |
|---|---|---|
| | Average | minimum–maximum |
| Invention product | 8'16" | 7'27"–9'45" |
| Control product | 3'53" | 3'26"–4'45" |

(Capsule number subjected to the test; 5)

Test - 4

Assessment of Disintegration Property

The hard capsule obtained in the Example of the present invention and the control gelatin hard capsule were filled with corn starch, and then subjected to the disintegration test under the standard condition defined by Japanese pharmacopoeia, using a first solution heated to 37°±1° C.

As shown in Tables 4 and 5, the disintegration of the hard capsule of the present invention is a bit slower than that of the control capsule, but the whole contents thereof were completely released within 3 to 5 minutes. Thus, it is confirmed that the hard capsule of the present invention is a hard capsule satisfactory for practical use.

TABLE 4

| Capsule | Capsule opening time | |
|---|---|---|
| | Average | minimum–maximum |
| Invention product | 2'43" | 1'47"–4'14" |
| Control product | 1'02" | 0'57"–1'08" |

(Capsule number subjected to the test; 6)

TABLE 5

| Capsule | Time for release completion of contents | |
|---|---|---|
| | Average | minimum–maximum |
| Invention product | 3'45" | 2'50"–4'55" |
| Control product | 2'03" | 1'58"–2'15" |

(Capsule number subjected to the test; 6)

The hard capsule for pharmaceutical drugs of the present invention contains as the base material a water-soluble cellulose derivative and further a gelatinizing agent and an auxiliary for gelation, and has the following features.

(1) A hard capsule of the lower content can be obtained, and furthermore, a capsule for pharmaceutical drugs with the film having an excellent mechanical strength can be provided.

(2) Due to the lower water content in equilibrium in the capsule film, pharmaceutical agents which are likely to be subjected readily to adverse effects of water can be filled in the hard capsule as they are, so that the formulation thereof into a capsule is easily done.

(3) Insolubility of the capsule film through the reaction with an aldehyde group or a carbonyl group never occurs.

(4) Because a gelatinizing agent and an auxiliary for gelation are used as auxiliary components of the base material, the hard capsule can be provided in inexpensive manner by using a hard capsule production system based on immersion method with no use of specified apparatuses or works.

What is claimed is:

1. A method for producing a hard capsule for pharmaceutical drugs, comprising preparing an aqueous solution of a capsule base containing a water-soluble cellulose derivative in the form of a cellulose ether in which some or all of the hydroxyl groups thereof are substituted with an alkyl group and/or a hydroxyalkyl group, a gelatinizing agent and an auxiliary for gelation, immersing a capsule molding pin in the aqueous solution of the capsule base, subsequently drawing out the molding pin from the aqueous solution of the capsule base, subjecting the aqueous solution of the capsule base attached to the outer surface of the molding pin to gelation at a temperature of 22.5° C. to 25.5° C., and forming a capsule film on the outer surface of the molding pin, wherein the solution temperature of the aqueous solution of the capsule base is 48° C. to 55° C.

2. The method for producing a hard capsule according to claim 1, wherein the solution temperature of the aqueous solution of the capsule base is 50° C. to 52° C.

3. The method for producing a hard capsule according to claim 1, wherein 5 to 25 parts by weight of the water-soluble cellulose derivative, 0.1 to 0.5 parts by weight of the gelatinizing agent and 0.01 to 0.5 parts by weight of the auxiliary for gelation are used in preparing the aqueous solution of the capsule base.

4. The method for producing a hard capsule according to claim 1, wherein the cellulose ether is selected from the group consisting of hydroxypropylmethyl cellulose, hydroxyethyl cellulose, hydroxypropyl cellulose, and hydroxyethylmethyl cellulose.

5. The method for producing a hard capsule according to claim 1, wherein the cellulose ether is hydroxypropymethyl cellulose.

6. The method for producing a hard capsule according to claim 1, wherein the gelatinizing agent is carrageenan and the auxiliary for gelation is a water-soluble compound containing potassium ion, ammonium ion or calcium ion.

7. The method for producing a hard capsule according to claim 6, wherein the carrageenan is selected from the group consisting of kappa-carrageenan, iota-carrageenan and ramda-carrageenan.

8. The method for producing a hard capsule according to claim 3, wherein 13 to 17 parts by weight of water-soluble cellulose derivative is used in preparing the aqueous solution of the capsule base.

9. The method for producing a hard capsule according to claim 3, wherein 0.15 to 0.3 parts by weight of the gelatinizing agent is used in preparing the aqueous solution of the capsule base.

10. The method for producing a hard capsule according to claim 3, wherein 0.05 to 0.2 parts by weight of the auxiliary for gelation is used in preparing the aqueous solution of the capsule base.

11. The method for producing a hard capsule according to claim 1, wherein the gelatinizing agent is selected from the group consisting of carrageenan, polysaccharide of tamarind seed, pectin, curdlan, gelatin, furcellaran and agar, and the auxiliary for gelation is a water-soluble compound containing potassium ion, ammonium ion or calcium ion.

* * * * *